United States Patent
Huggins, Jr.

(10) Patent No.: US 6,641,015 B2
(45) Date of Patent: Nov. 4, 2003

(54) REINFORCED ARTICLE HOLDER

(76) Inventor: Charles E. Huggins, Jr., P.O. Box 5757, Shreveport, LA (US) 71135

(*) Notice: Subject to any disclaimer, the term of this patent is extended or adjusted under 35 U.S.C. 154(b) by 17 days.

(21) Appl. No.: 09/922,259

(22) Filed: Aug. 6, 2001

(65) Prior Publication Data

US 2002/0020727 A1 Feb. 21, 2002

Related U.S. Application Data

(60) Provisional application No. 60/224,886, filed on Aug. 14, 2000.

(51) Int. Cl.$^7$ .................................................. A45C 1/04
(52) U.S. Cl. ..................... 224/674; 224/236; 224/251; 224/678
(58) Field of Search ................................ 224/251, 236, 224/674, 678, 679; 383/119

(56) References Cited

U.S. PATENT DOCUMENTS

| | | | | |
|---|---|---|---|---|
| 2,330,311 A | * | 9/1943 | Pierce | 493/217 |
| 2,712,337 A | * | 7/1955 | Tremblay | 206/315.1 |
| 3,370,773 A | * | 2/1968 | Mayo | 383/109 |
| 3,445,046 A | * | 5/1969 | Wilson | 224/148.5 |
| 3,568,918 A | * | 3/1971 | Blomqvist | 383/109 |
| 4,330,073 A | * | 5/1982 | Clark | 224/223 |
| 4,903,859 A | * | 2/1990 | Derby et al. | 383/41 |
| 4,913,326 A | | 4/1990 | Echelson | 224/222 |
| 5,100,051 A | * | 3/1992 | Triglia et al. | 229/87.19 |
| 5,215,379 A | | 6/1993 | Pickard et al. | 383/37 |
| 5,217,151 A | * | 6/1993 | Parsons | 224/672 |
| 5,263,619 A | * | 11/1993 | Shoemaker | 224/240 |
| 5,392,975 A | * | 2/1995 | Blankenship, Jr. | 224/148.5 |
| 5,443,192 A | * | 8/1995 | Hodges et al. | 224/148.6 |
| 5,477,999 A | | 12/1995 | Blankenship, Jr. | 224/253 |
| 5,711,468 A | * | 1/1998 | Shoemaker | 224/251 |
| 5,779,122 A | | 7/1998 | Martinelli | 224/683 |
| 5,833,093 A | | 11/1998 | Honaker et al. | 222/175 |
| 5,845,826 A | | 12/1998 | Nguyen | 224/222 |
| 5,855,307 A | | 1/1999 | Biddick et al. | 224/267 |

* cited by examiner

Primary Examiner—Stephen K. Cronin
(74) Attorney, Agent, or Firm—John M. Harrison

(57) ABSTRACT

A reinforced article holder suitable for containing auto-injector syringes, medications, first aid items or the like. In a preferred embodiment the reinforced article holder is typically a nylon holder body having a backing layer, an enclosure layer sewn to the backing layer and a holder interior between the layers. An elongated, tubular container for containing the syringe, medication or other article is removably inserted in the holder. An L-shaped reinforcing member, interposed between the backing layer and a cover layer which is sewn to the backing layer in the holder interior, maintains the holder body in a substantially rigid conformation and facilitates insertion of the container in the holder. A cover flap extends from the backing layer for selectively enclosing the container in the holder interior, and a belt loop is provided on the backing layer to facilitate carrying the holder body and enclosed container on a belt.

14 Claims, 2 Drawing Sheets

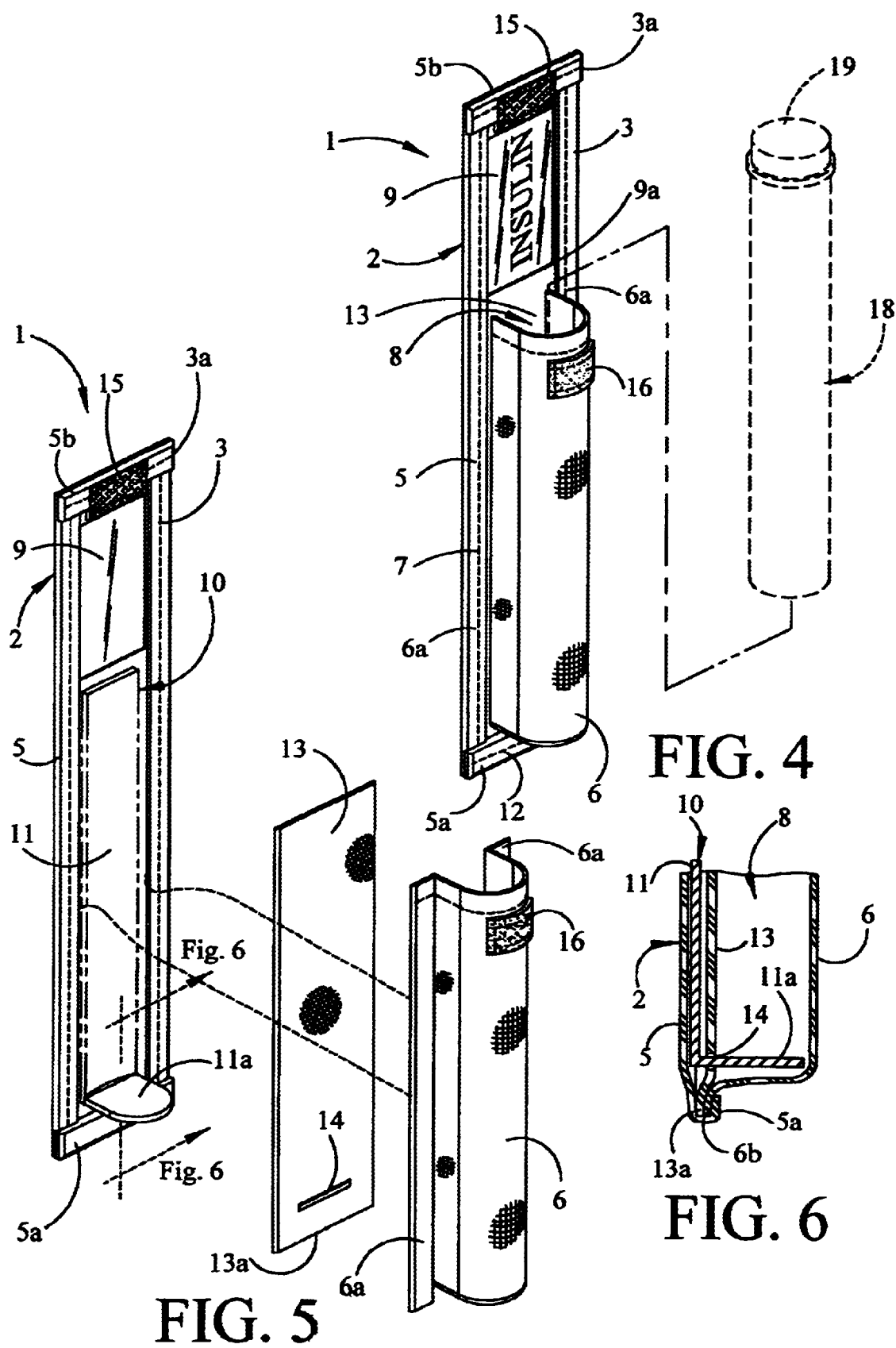

REINFORCED ARTICLE HOLDER

CROSS-REFERENCE TO RELATED APPLICATIONS

This application claims the benefit of now abandoned U.S. Provisional Application Serial No. 60/224,886, filed Aug. 14, 2000.

BACKGROUND OF THE INVENTION

1. Field of the Invention

This invention relates to pouches and holders for medications and syringes and the like and more particularly, to a reinforced article holder which is capable of safely containing auto-injector syringes, medications, first aid items or other articles and is typically carried on the belt of a user. In a preferred embodiment the reinforced article holder is characterized by a holder body having typically nylon backing and enclosure layers sewn to each other and a holder interior defined between the layers. An L-shaped reinforcing member is interposed between the backing layer and a nylon cover layer which is sewn to the backing layer in the holder interior. An elongated, tubular container for containing the syringe, medication or other article is removably inserted in the holder interior, and the reinforcing member maintains the holder body in a substantially rigid conformation to prevent inadvertent bending of the holder body as the container is inserted in the holder interior. The backing layer typically extends beyond the enclosure layer to define a flexible cover flap for selectively enclosing the container in the holder interior. A belt loop is typically provided on the backing layer to facilitate carrying the holder body and enclosed container on the belt of a user.

Persons who suffer from asthma, diabetes, allergies or other chronic illness must frequently carry appropriate medication or auto-injector syringes for self-administration according to a schedule or when necessary for the treatment or control of their condition. The medication or syringes are typically contained in an elongated, cylindrical or tubular syringe container which is inserted in a pouch carried on a belt or in a pocket of the person's clothing. The pouch is typically constructed of nylon or other flexible fabric material and thus, frequently tends to bend and become distorted through repeated use. This may render difficult insertion of the lightweight aluminum or plastic syringe or medication container into the pouch. Moreover, the container frequently becomes inserted too deep in the pouch in such a manner that the upper edge of the container is recessed in the pouch opening, thus rendering it difficult for the user to grasp and remove the container from the pouch. This problem becomes particularly acute under circumstances in which the patient is highly allergic to a certain substance and has a typically life-threatening systemic anaphylactic episode or allergic emergency upon exposure to the allergen. In such cases, epinephrine must be administered immediately to the patient to resolve the crisis, and the patient encounters difficulty in removing an auto-injector syringe containing the epinephrine from the pouch. Accordingly, a new and improved, reinforced article holder which imparts a rigid conformation to the holder for easy insertion of the container in the holder, and which limits the insertion depth of the container in the holder to enable quick and easy grasping and removal of the container therefrom, is needed.

2. Description of the Prior Art

Pouches or containers of various designs are known in the art for carrying articles such as medications, syringes or other articles. One of these containers is the "Armband Carrier for Audio Devices", described in U.S. Pat. No. 4,913,326, dated Apr. 3, 1990, to Echelson. The Echelson carrier includes an elastic sleeve designed to be worn on the upper arm, and an elastic band is sewn to the sleeve for receiving a portable radio. An "Information Storage Envelope" is detailed in U.S. Pat. No. 5,215,379, dated Jun. 1, 1993, to Pickard, et al. The envelope includes two pairs of straps for fastening the envelope to a post. The envelope interior is selectively closed by a cover flap provided with a window which receives a label for identifying the contents of the envelope. The weather-resistant envelope is used to contain printed material related to the sale of real estate, for example. U.S. Pat. No. 5,477,999, dated Dec. 26, 1995, to Blankenship, Jr., discloses a "Spray Container Carriage and Retrieval System", wherein a spray container having a forward trigger is stored in a specially-designed sleeve having a special surface for securing the trigger from the discharge position thereof. The surface is formed on a sleeve having a large bottom opening which admits displacement air. The sleeve is fitted with an upper flange which permits the sleeve to be carried in an open-bottomed holster. An "Asthma Medication Pouch" is described in U.S. Pat. No. 5,779,122, dated Jul. 14, 1998, to Martinelli, et al. The medication pouch includes a primary pouch for carrying at least one spray inhaler for an asthma patient, an elastic band provided on the primary pouch for carrying a syringe, an attaching apparatus for attaching the medication pouch to the belt, clothing or ankle of the patient, and a secondary pouch provided on the primary pouch for carrying asthma pills. A "Protective Cover for Small Spray Dispensers and Medicated Inhalers" is described in U.S. Pat. No. 5,833,093, dated Nov. 10, 1998, to Honaker, et al. The protective cover includes a rectangular base of a flexible material that can be folded on itself to form a closed cover and define a dispenser space. The base has outer and inner surfaces including hook-and-loop patches provided at each end of the base for latching the base in the closed cover form. An information card window is provided on the inner surface of the base. U.S. Pat. No. 5,845,826, dated Dec. 8, 1998, to Nguyen, details an "Arm Pouch Accessory and the Method for Using Same for the Delivery of Mail". The arm pouch accessory is characterized by an armband which fits on the arm of a mail carrier, and includes a pocket provided on the armband for receiving mail, a flap provided on the armband for selectively closing the pocket and a connector device for attaching the armband to a belt or other article of clothing of the mail carrier. An "Inhaler Holster" is disclosed in U.S. Pat. No. 5,855,307, dated Jan. 5, 1999, to Biddick, et al. The inhaler holster includes a wrist band having end hook and loop fasteners for holding an inhaler band to the wrist band, and a second set of hook and loop fasteners provided on the inhaler band hold an inhaler. The wrist band is generally perpendicular to the inhaler band, which either completely or partially encircles and holds the cannister containing the inhaler. The end segments of the cannister may be additionally secured to the inhaler band by operation of elastic strap assemblies attached to the inhaler band and which loop around the top and bottom of the cannister at opposite ends.

An object of this invention is to provide a new and improved, reinforced article holder for containing various selected items including auto-injector syringes, medications, first aid items or the like.

Another object of this invention is to provide a reinforced article holder which is characterized by rigidity and durability.

Still another object of this invention is to provide a bend-resistant, reinforced article holder designed to safely carry a syringe, medication, aspirin, gauze or other articles.

A still further object of this invention is to provide a reinforced article holder which is capable of carrying an epinephrine auto-injector syringe on the clothing of an individual and provides quick and easy access to the syringe to facilitate self-administration of the epinephrine in the event of a systemic anaphylactic crisis or allergic emergency.

Yet another object of this invention is to provide a reinforced article holder characterized by a holder body which removably receives a container or tube for holding a syringe, medication or other article and a reinforcing member which extends along the holder body for imparting rigidity and durability to the holder body and facilitating easy insertion of the container or tube in the holder body.

A still further object of this invention is to provide a reinforced article holder characterized by a holder body including a backing layer, an enclosure layer having an arcuate cross-section sewn to the backing layer and a holder interior defined between the backing layer and the arcuate enclosure layer for removably receiving a container which typically contains asthma or other medication or an auto-injector syringe containing insulin or epinephrine, and an elongated, L-shaped reinforcing or stiffening member which extends along the backing layer for substantially reinforcing the holder body and maintaining the holder body in a rigid configuration during insertion of the container in the holder interior, as well as maintaining the upper edge of the inserted container above the edge of the holder body opening to facilitate ease in grasping and removing the container from the holder body, as needed.

SUMMARY OF THE INVENTION

These and other objects of the invention are provided in a new and improved, reinforced article holder which is capable of safely containing auto-injector syringes, medications, first aid items such as gauze or bandages, or other articles and can be worn on the belt of a user for quick and convenient access to an auto-injector syringe or asthma medication in the holder, for example, as needed. In a preferred embodiment the reinforced article holder is characterized by a holder body having typically nylon backing and enclosure layers sewn to each other and a holder interior defined between the arcuate enclosure layer and the backing layer. An L-shaped reinforcing member is interposed between the backing layer and a nylon cover layer which is sewn to the backing layer in the holder interior, and extends along the backing layer. An elongated, tubular container for containing the syringe, medication, first aid items or other articles is removably inserted in the holder interior, and the reinforcing member maintains the holder body in a substantially rigid conformation and prevents inadvertent bending of the holder body as the container is inserted in the holder interior. The L-shaped reinforcing member includes a bottom flange for limiting the depth of insertion of the container in the holder interior and thus, preventing the container from recessing in the pouch opening. The backing layer typically extends beyond the enclosure layer to define a flexible cover flap for engaging the enclosure layer and selectively enclosing the container in the holder interior. A belt loop is typically provided on the backing layer to facilitate carrying the holder body and enclosed container on the belt of a user.

BRIEF DESCRIPTION OF THE DRAWINGS

The invention will be better understood by reference to the accompanying drawings, wherein:

FIG. 4 is a perspective view of the reinforced article holder, more particularly illustrating removable insertion of the syringe tube container component of the holder in the holder body of the reinforced article holder;

FIG. 5 is an exploded, perspective view of the reinforced article holder; and

FIG. 6 is a sectional view, taken along section lines 6—6 in FIG. 5, of the reinforced article holder.

DESCRIPTION OF THE PREFERRED EMBODIMENTS

Figure 1:
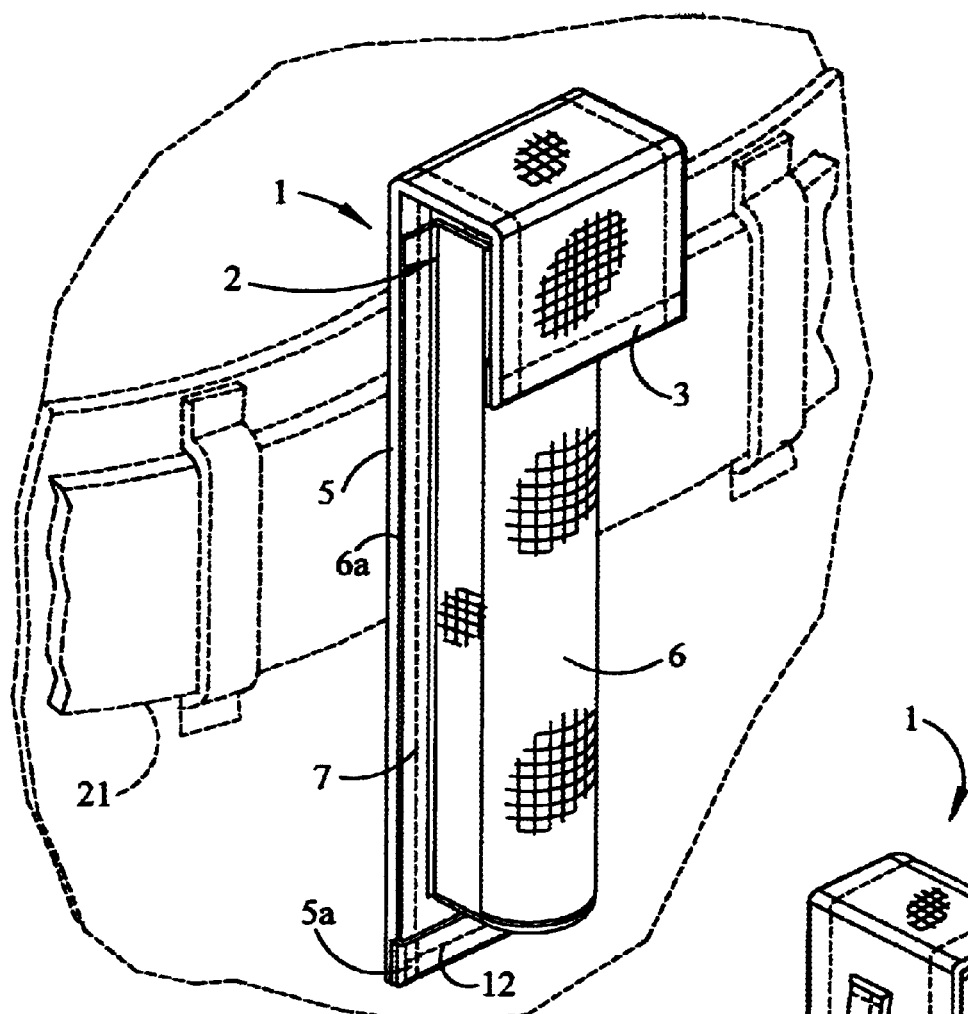
FIG. 1 is a perspective view of a preferred embodiment of the reinforced article holder of this invention, carried on the belt (in phantom) of a user in typical application of the reinforced article holder.
Figure 3:
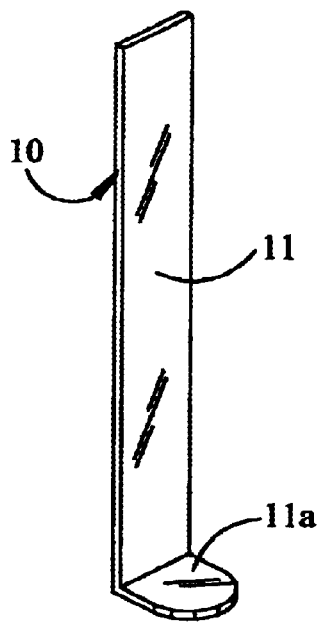
FIG. 3 is a perspective view of the reinforcing member component of the reinforced article holder.
Figure 2:
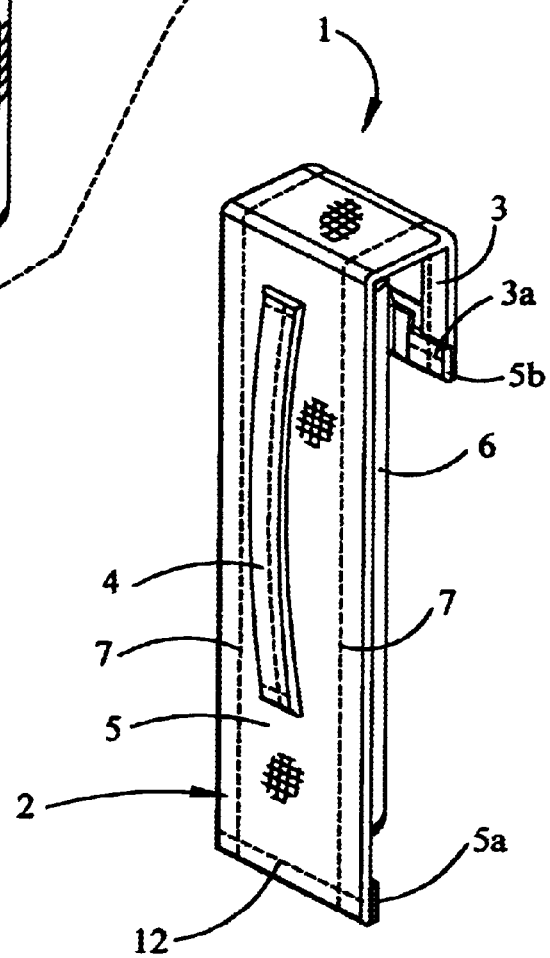
FIG. 2 is a rear, perspective view of the reinforced article holder illustrated in FIG. 1.

Referring to the drawings, the reinforced article holder of this invention is generally illustrated by reference numeral 1. The reinforced article holder 1 is characterized by a holder body 2 which is typically constructed of nylon and includes an elongated, rectangular backing layer 5, as well as an elongated enclosure layer 6 having an arcuate cross-section and edges 6a which are stitched to the backing layer 5 at side seams 7, as illustrated in FIG. 4. An elongated, rectangular cover layer 13, having an elongated, transverse flange slot 14 adjacent and substantially parallel to the bottom edge 13a thereof as illustrated in FIG. 5, is interposed between the backing layer 5 and the enclosure layer 6, and is stitched to the backing layer 5 and the edges 6a of the enclosure layer 6 at the side seams 7. As illustrated in FIG. 6, a bottom fold 5a is formed along the bottom edge of the backing layer 5. The bottom edge 6b of the enclosure layer 6 and the bottom edge 13a of the cover layer 13 are each typically inserted in the bottom fold 5a of the backing layer 5, and stitched to the bottom fold 5a at a bottom seam 12 (FIG. 4). A holder interior 8 is defined between the arcuate enclosure layer 6 and the cover layer 13. In application of the reinforced article holder 1 as hereinafter described, an elongated, typically cylindrical, metal or plastic syringe tube 18 (illustrated in phantom in FIG. 4), fitted with a removable cap 19, is removably inserted in the holder interior 8 and contains an insulin or epinephrine auto-injector syringe, medication, aspirin, first aid items or other articles. The upper portion of the backing layer 5 extends beyond the enclosure layer 6 and the cover layer 13 to define a flexible cover flap 3, the upper edge of which is typically folded to define a top fold 5b, secured by a top seam 3a. The top fold 5b is typically provided with a pile element 15 of a loop-pile fastener for removably engaging a companion loop element 16 of the loop-pile fastener, provided on the enclosure layer 6, and selectively closing the holder interior 8, as hereinafter further described. It is understood that other fastening elements such as snaps, in non-exclusive particular, can be provided on the cover flap 3 and enclosure layer 6, respectively, of the holder body 2 for securing the cover flap 3 against the enclosure layer 6 and selectively closing the holder interior 8. A transparent, plastic label window 9 is typically provided on the cover flap 3, above the holder interior 8 and, as illustrated in FIG. 4, receives a label 9a having "INSULIN", as illustrated, or other descriptive indicia printed thereon, for purposes which will be hereinafter described. As illustrated in FIG. 2, in a preferred embodiment a belt loop 4 is typically sewn on the backing layer 5 of the holder body 2 to facilitate carrying the reinforced article holder 1 on the belt 21 of a user, in typical application of the reinforced article holder 1 as illustrated in FIG. 1 and hereinafter further described.

As further illustrated in FIGS. 5 and 6, the elongated portion 11 of a reinforcing member 10, typically constructed of metal or a rigid plastic material, is interposed between the cover layer 13 and the backing layer 5 of the holder body 2. The elongated portion 11 of the reinforcing member 10 is substantially coextensive with the enclosure layer 6 and the cover layer 13 of the holder body 2 and extends along the backing layer 5. A flange 11a extends from the elongated portion 11 in substantially perpendicular relationship thereto at the bottom end of the elongated portion 11, and extends through the flange slot 14 of the cover layer 13 as illustrated in FIG. 6 for purposes which will be hereinafter described.

Referring again to FIGS. 1 and 4 of the drawings, in typical application of the reinforced article holder 1, the holder body 2 is typically mounted on the belt 21 (illustrated in phantom in FIG. 1) of a user by extending the belt 21 through the belt loop 4 (FIG. 2) of the holder body 2. The syringe tube 18, typically containing an insulin or epinephrine auto-injector syringe, asthma medication, first aid items such as gauze or bandages, or other articles (not illustrated), is inserted downwardly into the holder interior 8 of the holder body 2, until the bottom of the syringe tube 18 contacts and rests on the flange 11a (extending through the flange slot 14 of the cover layer 13, FIG. 6) of the reinforcing member 10. As the syringe tube 18 is inserted in the holder interior 8, the elongated portion 11 of the reinforcing member 10 prevents inadvertent bending of the holder body 2 and thus, facilitates quick and easy insertion of the syringe tube 18 in the holder interior 8. It will be appreciated by those skilled in the art that when the syringe tube 18 is fully inserted in the holder interior 8, with the bottom of the syringe tube 18 resting on the flange 11a of the reinforcing member 10, the cap 19 of the syringe tube 18 protrudes through the opening of the holder interior 8 to facilitate grasping and pulling the syringe tube 18 from the holder interior 8, as needed. The cover flap 3 is bent downwardly, and the pile element 15 (provided on the cover flap 3) of the loop-pile fastener is caused to engage the companion loop element 16 (provided on the enclosure layer 6) of the loop-pile fastener to facilitate enclosing the syringe tube 18 in the holder interior 8 while the reinforced article holder 1 is carried on the belt 21 of the user. When it is necessary to retrieve the syringe, medicine, first aid items or other articles (not illustrated) from inside the syringe tube 18, the cover flap 3 is opened to expose the protruding cap 19 of the syringe tube 18 by disengaging the pile element 15 from the companion loop element 16 of the loop-pile fastener, and lifting the cover flap 3. The cap 19, protruding through the opening of the holder interior 8, is then easily grasped and the syringe tube 18 pulled from the holder interior 8, and the syringe, medicine, first aid items or other contents of the syringe tube 18 removed from the syringe tube 18 after removing the cap 19 therefrom. A paper or plastic label 9a, bearing identifying insignia such as "INSULIN", as illustrated, is typically inserted between the label window 9 and the cover flap 3 for identifying the contents of the container 18.

It will be appreciated by those skilled in the art that the reinforced article holder of this invention is useful for safely carrying insulin or epinephrine auto-injector syringes, asthma or other medications or pills, aspirin, gauze, bandages or other articles, and facilitates quick and easy retrieval of the holder contents when needed. This capability is particularly advantageous under circumstances in which the user of the reinforced article holder experiences an episode of systemic anaphylaxis, in which case an epinephrine auto-injector contained in the syringe tube can be quickly removed from the reinforced article holder and administered to the user. It is understood that the holder body can be constructed of a variety of suitable materials other than nylon, including polyester and polypropylene, in non-exclusive particular, and the reinforcing member is effective for preventing inadvertent bending of the holder body which would otherwise render difficult or cumbersome insertion of the syringe tube in the holder interior.

While the preferred embodiments of the invention have been described above, it will be recognized and understood that various modifications can be made in the invention and the appended claims are intended to cover all such modifications which may fall within the spirit and scope of the invention.

Having described my invention with the particularity set forth above, what is claimed is:

1. A reinforced article holder for holding articles, comprising a holder body; a container for containing the articles and removable insertion in said holder body; and a reinforcing member having an elongated portion disposed along said holder body and a flange carried by said elongated portion for limiting insertion of said container in said holder body and maintaining said holder body in a substantially rigid conformation upon insertion of said container in said holder body.

2. The reinforced article holder of claim 1 wherein said holder body comprises a backing layer, an enclosure layer provided on said backing layer and a holder interior defined between said backing layer and said enclosure layer for receiving said container.

3. The reinforced article holder of claim 1 wherein said container comprises an elongated tube and a cap removably fitted on said tube.

4. The reinforced article holder of claim 3 wherein said holder body comprises a backing layer, an enclosure layer provided on said backing layer and a holder interior defined between said backing layer and said enclosure layer for receiving said container.

5. The reinforced article holder of claim 1 comprising a belt loop provided on said holder body.

6. The reinforced article holder of claim 5 wherein said holder body comprises a backing layer, an enclosure layer provided on said backing layer and a holder interior defined between said backing layer and said enclosure layer for receiving said container.

7. A reinforced article holder for holding articles, comprising a holder body having a backing layer, an enclosure layer provided on said backing layer, a holder interior defined between said enclosure layer and said backing layer and a cover layer provided on said backing layer in said holder interior; a reinforcing member provided in said holder body for reinforcing said holder body, said reinforcing member comprising an elongated portion disposed between said backing layer and said cover layer and a flange carried by said elongated portion; and a container for containing the articles and removable insertion in said holder interior of said holder body, whereby said reinforcing member maintains said holder body in a substantially rigid configuration upon insertion of said container in said holder interior and said flange limits insertion of said container in said holder interior.

8. The reinforced article holder of claim 7 wherein said container comprises an elongated tube and a cap removably fitted on said tube.

9. The reinforced article holder of claim 7 comprising a belt loop provided on said holder body.

10. The reinforced article holder of claim 9 wherein said container comprises an elongated tube and a cap removably fitted on said tube.

11. A reinforced article holder for holding articles, comprising a holder body having a backing layer, an enclosure layer provided on said backing layer, a holder interior defined between said enclosure layer and said backing layer and a cover layer provided on said backing layer in said holder interior; a reinforcing member provided in said holder body for reinforcing said holder body, said reinforcing member comprising an elongated portion disposed between said backing layer and said cover layer and a flange disposed in substantially perpendicular relationship to said elongated portion; a container for containing the articles and removable insertion in said holder interior of said holder body, whereby said reinforcing member maintains said holder body in a substantially rigid conformation upon insertion of said container in said holder interior and said flange limits insertion of said container in said holder interior; and a cover flap carried by said backing layer for selectively closing said holder interior.

12. The reinforced article holder of claim 11 wherein said container comprises an elongated tube and a cap removably fitted on said tube.

13. The reinforced article holder of claim 11 comprising a belt loop provided on said holder body.

14. The reinforced article holder of claim 13 wherein said container comprises an elongated tube and a cap removably fitted on said tube.

* * * * *